US007682317B2

(12) United States Patent
Bowman et al.

(10) Patent No.: US 7,682,317 B2
(45) Date of Patent: Mar. 23, 2010

(54) SYSTEM FOR ASSESSING ENDOTHELIAL FUNCTION BASED ON TISSUE PERFUSION VALUES

(75) Inventors: Harry Frederick Bowman, Needham, MA (US); Gregory T. Martin, Cambridge, MA (US)

(73) Assignee: Thermal Technologies, Inc., Cambridge, MA (US)

( * ) Notice: Subject to any disclaimer, the term of this patent is extended or adjusted under 35 U.S.C. 154(b) by 702 days.

(21) Appl. No.: 10/407,318

(22) Filed: Apr. 3, 2003

(65) Prior Publication Data

US 2003/0191395 A1    Oct. 9, 2003

Related U.S. Application Data

(60) Provisional application No. 60/370,566, filed on Apr. 5, 2002.

(51) Int. Cl.
*A61B 5/00* (2006.01)
*A61B 5/02* (2006.01)
(52) U.S. Cl. ..................... 600/549; 600/504
(58) Field of Classification Search ........... 600/504, 600/549, 555; 606/27, 28; 607/96, 112
See application file for complete search history.

(56) References Cited

U.S. PATENT DOCUMENTS

| 4,059,982 | A | | 11/1977 | Bowman | |
|---|---|---|---|---|---|
| RE30,317 | E | * | 7/1980 | Lubbers et al. | 600/363 |
| 4,228,805 | A | * | 10/1980 | Rosen et al. | 600/504 |
| 4,569,355 | A | * | 2/1986 | Bitterly | 600/504 |
| 4,852,027 | A | | 7/1989 | Bowman et al. | |
| 4,859,078 | A | | 8/1989 | Bowman | |
| 5,769,784 | A | * | 6/1998 | Barnett et al. | 600/300 |
| 6,152,881 | A | * | 11/2000 | Raines et al. | 600/507 |
| 6,221,025 | B1 | * | 4/2001 | Skoletsky | 600/504 |
| 6,248,066 | B1 | | 6/2001 | Barnett et al. | |
| 6,277,082 | B1 | | 8/2001 | Gambale | |
| 6,322,515 | B1 | | 11/2001 | Goor et al. | |
| 6,445,945 | B1 | | 9/2002 | Arsenault | |
| 6,488,623 | B1 | * | 12/2002 | Ozarowski et al. | 600/363 |
| 6,939,304 | B2 | * | 9/2005 | Schnall et al. | 600/481 |
| 2002/0090341 | A1 | | 7/2002 | Watson et al. | |

OTHER PUBLICATIONS

Anderson, TJ. Assessment and treatment of endothelial dysfunction in humans. J. Am. Coll. Cardiol. 1999;34;631-638.*
A Thermal Conductivity Sensor for the Measurement of Skin Blood Flow A. Dittmar, T. Pauchard and G. Delhomme.

* cited by examiner

*Primary Examiner*—Max Hindenburg
*Assistant Examiner*—Jonathan M Foreman
(74) *Attorney, Agent, or Firm*—James L. Neal

(57) ABSTRACT

The system assesses the endothelial function of a subject. Particularly, peripheral tissue perfusion measurements taken in a subject are compared to reference perfusion data and the comparison yields the assessment of endothelial function. The reference may be data indicative of peripheral tissue perfusion in a healthy person. Also, peripheral tissue perfusion measurements taken in a subject when perfusion is in an unperturbed state (the reference) can be compared to perfusion measurements taken promptly after a challenge to normal or unperturbed tissue perfusion of the subject.

5 Claims, 6 Drawing Sheets

SYSTEM FOR ASSESSING ENDOTHELIAL FUNCTION BASED ON TISSUE PERFUSION VALUES

PRIORITY CLAIM

This application claims priority from commonly owned U.S. Provisional Application Ser. No. 60/370,566, filed 5 Apr. 2002.

BACKGROUND OF THE INVENTION

Atherosclerosis is a leading cause of death and disability. Atherosclerosis is the narrowing of an artery lumen by an accumulation of "plaque" consisting of fat, cholesterol, calcium, cells and/or fibrin on the inside wall of the artery. The accumulation of plaque results in ischemia, an insufficient blood supply to meet the metabolic needs of an affected tissue bed. This can lead to heart attack, congestive heart failure, arrhythmia, stroke, kidney failure and loss of limbs.

Plaque accumulation in cerebral arteries can lead to transient ischemic events when blood flow is reduced to critical cerebral tissues. This can produce a form of ischemic stroke called thrombotic stroke. Symptoms are weakness, dizziness, confusion, slurred speech and vision impairment. These symptoms may not be severe and are temporary but they indicate that the patient is at risk for a more serious ischemic stroke.

Atherosclerosis also occurs in the peripheral arteries that feed the extremities. This can cause symptoms such as pain, numbness, ulcers and difficulty walking. Though these are seldom life threatening they do degrade the quality of life.

A screening technique is needed which will permit direct, non-invasive or minimally invasive diagnosis of atherosclerosis or of the predisposition of a patient to atherosclerosis. A number of techniques are available to diagnose atherosclerosis when there is advanced blood vessel blockage. They include angiography, magnetic resonance angiography and Doppler ultrasound. Angiography is invasive but provides an accurate image of any blockage. It is often used to diagnose atherosclerosis in coronary and cerebral arteries. Magnetic resonance angiography is less available and less accurate than angiography. Doppler ultrasound is non-invasive and can be used in most peripheral vasculature. Its use in cerebral vasculature is somewhat limited. Each of these techniques detects or quantifies advanced atherosclerosis. They fail, however, to detect progressive atherosclerosis in early stages during decades of disease progression when a subject is free of symptoms and prior to the onset of major health impairment.

The arterial lumens throughout the body are lined with endothelial cells. The intact endothelium regulates a variety of physiologic functions including vasoconstriction and vasodilatation. Endothelial cells become damaged in the initial stage of atherosclerosis, decades before the development of obstructing plaque and clinical vascular disease. Damaged endothelial cells fail in a number of roles including physiologic vasodilatation. Traditional risk factors for atherosclerosis, including hypertension, smoking, diabetes and hypercholesterolemia, are all associated with impaired endothelial function. A linear relationship between endothelial dysfunction and atherosclerosis has been reported. (A. M. Zeiher, H. Drexler, H. Wollschlager, H. Just, "Modulation of the Coronary Vasomotor Tone in Humans: Progressive Endothelial Dysfunction with Different Early Stages of Atherosclerosis", Circulation 1991; 83:391-401.) Diagnosis of endothelial dysfunction could expand the use of therapies known to decrease cardiovascular events. In patients with diagnosed cardiovascular disease an endothelial evaluation could be used to judge the efficacy of therapeutic interventions.

Non-invasive evaluation of endothelial function has been a challenging endeavor. One of the most commonly employed non-invasive techniques is brachial artery reactivity. With this technique blood flow is challenged mechanically or pharmaceutically and afterward the reactive augmented arterial flow is measured. For example, the subject's upper arm may be occluded for about five minutes by inflation of a blood pressure cuff and then released by deflation of the cuff. Deflation of the cuff results in a substantial transient increase in blood flow. After deflation, the brachial artery diameter is measured with a two-dimensional ultrasound and Doppler ultrasound. Measurements recorded at baseline are compared with reactive augmented flow occurring after deflation of the blood pressure cuff Healthy subjects are found to experience about a twenty percent increase in brachial artery diameter and about a sixty percent increase in blood flow. With endothelial dysfunction, vessel diameter may increase five percent or less and the subject may experience an increase in blood flow of less than twenty-five percent. The test is accurate when performed in dedicated research laboratories in small numbers of patients. However, this technique requires expensive ultrasound equipment, an experienced ultrasonographer and approximately forty-five to sixty minutes per exam.

SUMMARY OF THE INVENTION

It is an object of this invention to provide an easy-to-use system for assessing atherosclerotic vascular disease in a subject.

An object of this invention is to assess endothelial function as a surrogate for atherosclerotic vascular disease.

It is a purpose of this invention to provide an easy-to-use system for assessing the risk of atherosclerotic vascular disease prior to a patient being symptomatic by measuring tissue perfusion to assess endothelial function as a surrogate for atherosclerotic vascular disease.

It is a purpose of this invention to provide a non-invasive measure of peripheral tissue perfusion to assess endothelial function as a surrogate monitor of atherosclerotic vascular disease.

A further purpose of this invention is to provide a non-invasive thermal sensor for the assessment of tissue perfusion.

A physiological parameter that correlates with endothelial function is measured to give an indication of the endothelial function of a subject. Peripheral tissue perfusion is one such parameter. Perfusion is the rate at which the quantity of blood in a given mass or volume of tissue is replenished at the level of the capillary network. The characteristics of peripheral tissue perfusion are directly affected by endothelial function. The measurement of peripheral tissue perfusion thus can be used as a proxy to assess endothelial function, which serves as a surrogate monitor of atherosclerotic vascular disease.

Tissue perfusion is assessed over a time interval. The characteristics of the perfusion data collected over the interval are compared to reference data. The reference data may be a model or standard data set that relates tissue perfusion known to be typical of a healthy person to endothelial function. The reference data also may be data collected from the subject at the time of the examination. For example, a selected physiological parameter that is related to the endothelial function (e.g.: perfusion) is challenged when in an initial, unperturbed state. Parameter characteristics and values before and after the challenge are assessed and compared. Changes in the characteristics of the parameter induced by the challenge are used to characterize endothelial function. Measurements of parameter characteristics or values after the challenge are, in one case, compared to a reference that may be a standard data set known to be typical of a person with healthy endothelial function. Alternately, a measurement made in the subject prior to the challenge is compared to a measurement after the challenge and in this case the prior measurement is the reference. Various physical and pharmacological challenges are possible. The kind and magnitude of changes induced will depend on the parameter and challenge chosen.

In one embodiment, a perfusion measurement is made over a brief interval at a selected tissue site and, after the measurement, blood flow to the site is mechanically constricted for an interval and then released. A second perfusion measurement is taken over a brief interval at the same site upon release of the constriction and compared to the first measurement. Differences in perfusion related values measured are an indicator of endothelial function and vascular health.

Blood flow to the site of the measurement may be chemically challenged systemically or locally using such pharmaceuticals and chemicals as nitroglycerine and acetylchlorine.

One of the characteristics of perfusion data collected that is an indicator of the state of the subject's endothelial function is the hyperemic response that occurs after a quick release of a challenge to tissue blood flow. A pronounced hyperemic response to release of the challenge and, correspondingly, a transient perfusion value after release that is substantially higher than the value of a perfusion measurement made before constriction of the blood flow indicates a subject without peripheral vascular disease. In contrast, an incomplete hyperemic response and a corresponding lower (or less high) transient perfusion value at the site after release indicates a subject with coronary artery disease. Typically in patients with coronary artery disease the perfusion related value after release of the constriction will be near or below the initial perfusion measurement value. Perfusion values resulting from the measurements may be absolute or relative. Relative values provide good data because the significant information is the difference in the perfusion values before and after the challenge to peripheral blood flow.

When peripheral tissue perfusion (or blood flow) data that corresponds to a known (e. g. healthy) endothelial function is used as a standard, the standard may be used in lieu of dual measurements in the subject at the time of the examination.

A non-invasive thermal sensing device suitable for use in connection with this invention is based on a transducing system capable of transmitting thermal energy to a selected tissue site and detecting the thermal response of the tissue to the application of thermal energy. One embodiment of the invention uses a thermal transducer in the form of a thermistor to both transmit thermal energy to tissue and sense the thermal response of the tissue to the energy transmitted. The thermal response of tissue to the application of thermal energy is a function of the perfusion at the site of application.

One embodiment of a perfusion sensor that can be used in connection with this invention has a thermal transducer supported within a surrounding mounting structure. The mounting structure supports the transducer for presentation to the skin surface. When the mounting structure is placed in contact with the skin surface, the transducer contacts the skin surface and force is applied to the transducer of a magnitude effective to establish thermal contact between the transducer and the skin surface and ineffective to cause collapse of the underlying capillary bed. The skin-contacting contacting surfaces of the mounting structure may be spaced outward from the transducer a distance sufficient to be outside the area (or volume in the case of an invasive sensor) that is materially affected by thermal energy from the transducer (i.e.: outside the thermal response zone of the transducer) when the transducer is in thermal contact with the skin surface. Perfusion is calculated as a function of the thermal response of the tissue to the application of heat. Various systems capable of applying thermal energy to tissue and detecting the resulting thermal response of the tissue can be used. For example, the system described in U.S. Pat. No. 4,852,027, issued Jul. 25, 1989, to Bowman et al.

The mounting structure that supports the transducer may include a resilient device such as a spring or elastomeric mount for applying a predetermined pressure to the transducer. When the mounting structure is applied to a skin surface the requisite force is applied to the transducer to establish thermal contact between the transducer and the skin surface without causing collapse of the underlying capillary bed. Alternately, an adjustable mount may be employed to vary the force applied to the transducer in accordance with different skin surface and capillary bed conditions. One such adjustable mount uses an inflatable or balloon-like member installed within the surrounding mounting structure. The transducer is affixed to the inflatable member so that it is in contact with the skin surface when the mounting structure is applied to the skin surface. The member is inflated more or less to cause the transducer to transmit more or less pressure, respectively, to the skin surface and the underlying capillary bed. Also, the device could be equipped with a sensor for sensing the skin contact pressure and adjusting the inflation of the inflatable member to optimize the pressure applied by the transducer to the skin surface. In each circumstance, the thermistor or other thermal transducer is to be in effective thermal contact with the skin surface of a subject but not under a force sufficient to produce pressure on the skin surface which will collapse the underlying capillary bed.

The sensing device is located on the surface of the skin of a patient at a site where perfusion measurements are to be made and the transducer or thermistor, in thermal contact with the underlying tissue, transmits thermal energy to the skin surface and the underlying capillary bed. The thermistor or other suitable thermal sensor senses the perfusion-dependent thermal response of the skin and underlying capillary bed to the introduction of thermal energy.

In cases where blood flow to a tissue site is challenged, the initial perfusion measurement will be taken when the perfusion at the site is at an unperturbed value. For example, the thermal perfusion sensing device can be located at a site on the forearm of a subject to obtain an initial perfusion value that will correspond to the unperturbed perfusion at that site. Blood flow to the site is then constricted for an interval by inflating a blood pressure cuff on the upper arm of the subject. The blood pressure cuff is deflated at the end of the interval and the normal hyperemic response produces a sudden increase in perfusion to the arm. A second perfusion measurement is made at the site immediately after the cuff is deflated to measure the hyperemic response. Initial and final perfusion related values are compared. Typically the increase in perfusion after deflation of the cuff will be relatively large in a patient without compromised endothelial function and muted or relatively small in a patient with compromised endothelial function. A final value substantially above the initial value is one indicator of good endothelial function and an absence of significant atherosclerotic vascular disease or coronary artery disease. A final perfusion value below or not substantially above the initial value is one indicator of poor endotheial function and the presence of atherosclerotic vascular disease or coronary artery disease.

A thermistor based perfusion sensor of the type described in U.S. Pat. No. 4,852,027 issued to Bowman et al. can be used in connection with this invention non-invasively or in a minimally invasive mode. In the invasive mode the sensor is introduced into peripheral tissue and senses perfusion related values in the surrounding capillary bed. Systems using a non-invasive sensor are painless to the subject, simple to use and do not require a skilled operator.

DETAILED DESCRIPTION OF THE DRAWINGS

Figure 1:
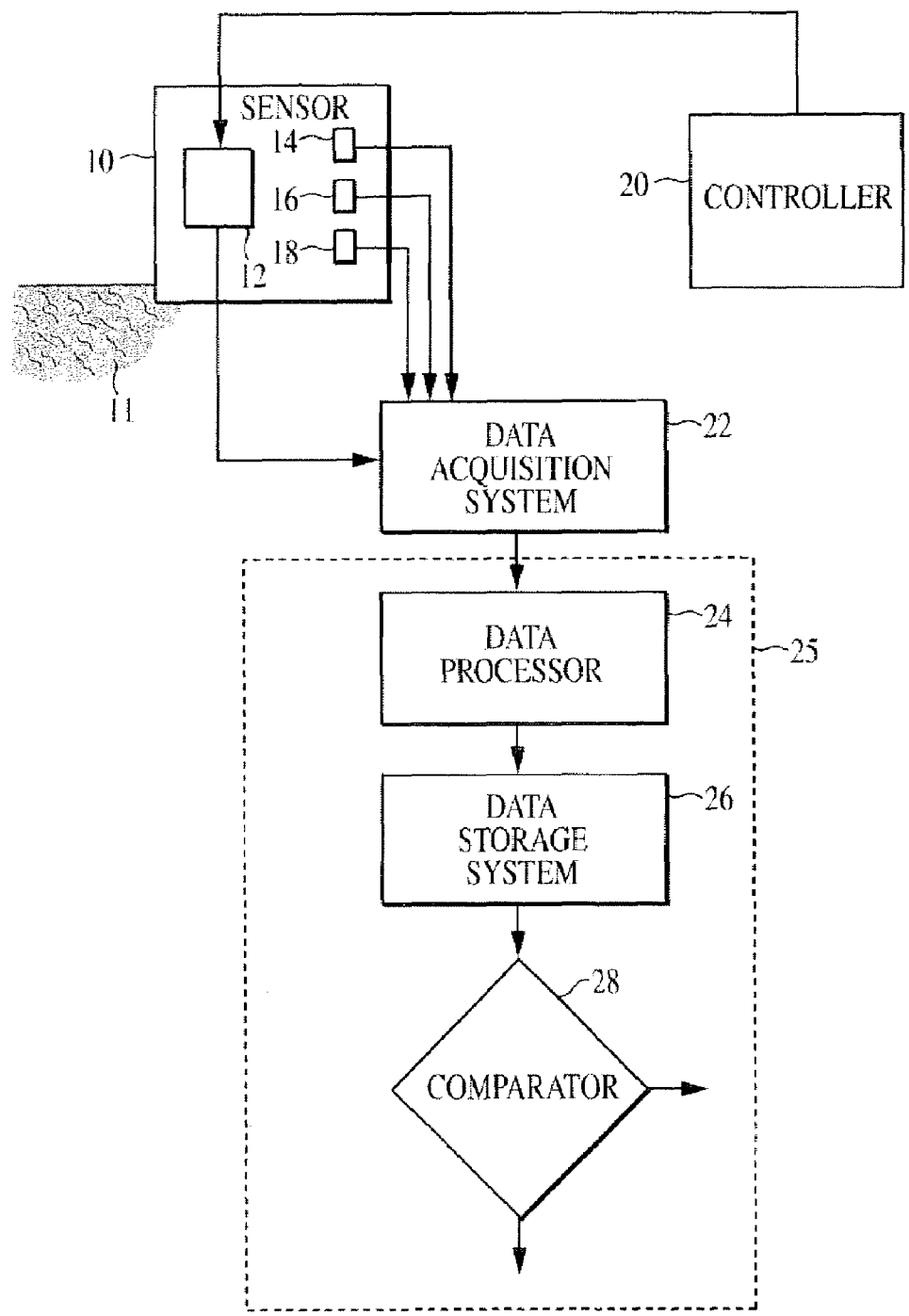
FIG. 1 illustrates a system according to one embodiment of the invention.

According to the embodiment of the invention illustrated by FIG. 1, a sensor 10 is applied to the skin surface at a selected location on a living subject, for example, on the forearm of the subject. In one embodiment of the invention the sensor is noninvasive and is applied so that a thermal transducer, for example a self-heating thermistor 12, and the baseline temperature sensors 14, 16 and 18 are in effective thermal contact with the skin surface. (Further characteristics of non-invasive sensors useful in connection with this invention will be discussed in connection with FIGS. 8, 9 and 10.)

When the thermal transducer or thermistor 12 is in thermal contact with the skin surface, the controller 20 energizes the thermistor 12 to raise its temperature to a selected level above its initial equilibrium level. The maximum temperature in the capillary bed heated by the thermistor 12 occurs at the contact site of the thermistor and decreases in all directions therefrom to the baseline or reference temperature. That is, the capillary bed temperature decreases to the baseline temperature of unheated tissue surrounding the site of the thermistor 12. The skin surface and underlying tissue surrounding the site of the thermistor within which the temperature is elevated to any substantial extent is the interrogation volume or thermal response zone of the thermistor. The rate at which heat is transferred from the thermistor 12 is a function of the effective thermal conductivity of tissue within the thermal response zone. The effective thermal conductivity of living tissue has two principal components, tissue perfusion (i.e.: the effect of convection or blood flow in the tissue) and the intrinsic thermal conductivity of the tissue. The power that is dissipated in maintaining the temperature of the thermistor 12 at the selected elevated level is dependent upon the effective thermal conductivity of tissue within the thermal response zone of the thermistor. More particularly, the power dissipated is a function of tissue perfusion in the thermal response zone of the thermistor.

The system of FIG. 1 is described as follows. The thermistor 12 is energized by power from an electrical power source in the control circuit 20 when a selected physiological parameter related to the endothelial function of a subject, in this case perfusion, is at an initial, unperturbed state. The energized thermistor 12 heats the adjacent capillary bed 11. The rate at which the heat energy is conducted away from the capillary bed and thus away from the thermistor 12 is a function of the rate of perfusion in the tissue forming the capillary bed. Thermal sensors 14, 16 and 18 are located to be outside the thermal response zone of the thermistor 12 and surround the tissue in the thermal response zone to sense the baseline temperature of tissue outside and around the thermal response zone. The data processing system 25 processes data from the thermistor 12 and sensors 14, 16 and 18 to provide a perfusion related value for tissue in the capillary bed 11. Specifically, data from the thermistor 12 and the sensors 14, 16 and 18 are collected by the data acquisition system 22 and forwarded to the data processor 24. The data collected at the site of the thermistor 12 is used by the data processor 24 to calculate a perfusion related value corresponding to perfusion in the thermal response zone of the thermistor 12 during an initial, unperturbed physiological condition. The calculated perfusion value for the initial physiological state is stored by data storage system 26 for further processing. In circumstances where baseline temperature shifts will substantially degrade the calculated perfusion value, data from the sensors 14, 16 and 18 can be used to compensate for the baseline temperature shifts. An intervention induces a change or perturbation in the state of the selected physiological parameter, in this case perfusion. A second perfusion related value is calculated by the data processor 24 for the changed state of perfusion. The stored perfusion value for the initial state is accessed and compared to the second calculated perfusion value. The differential value provides an indicator of endothelial function and the vascular health of the subject. Examples of data values that may be an indicator are hyperemic response, vasomotor activity and, when the data are displayed as a curve, the slope, amplitude and mean values of the curve. Examples of the manner in which a difference in perfusion values correlate with endothelial function will be described below in connection with FIG. 7.

The attending physician may observe the values calculated before and after the intervention and on the basis of the comparison make a judgment regarding the health of the subject's endothelium. Also, the comparator 28 may produce a comparison of the first and second calculated values to provide "yes" and "no" indicia or numerical indicia which can be displayed as qualitative values relating to endothelial function. An index of endothelial function may be used in which numbers from 10 to 1 indicate respectively good to poor endothelial function. Before and after difference values in one value range would result in an index value of 10. Before and after difference values in another range would result in a number 9 and so on to number 1. Other data relating to endothelial function also may be displayed.

A more encompassing endothelial index can be developed using a weighted combination of endothelial function related variables. For example, in an initial, unperturbed state one or more variables can be assessed. Examples of such variables are level of flow (perfusion), the natural frequency response of blood flow to perturbation, temperature at the skin surface, fluctuations in tissue temperature and the temperature difference between the maximum temperature in the thermal response zone and the baseline temperature. After a challenge to blood flow or other perturbation, the values of the same variables can be compared to their pre-perturbation values. Comparisons can be intermittent or continuous. A profile of values with time can be displayed to facilitate comparison or a data-processed comparison can be displayed directly.

Figure 2:
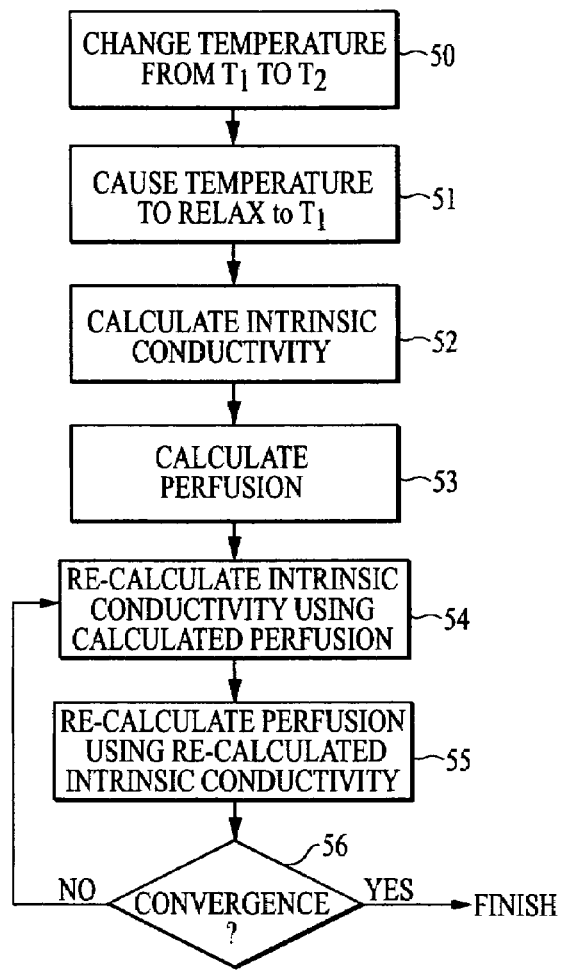
FIG. 2 is a flow chart illustrating an exemplary perfusion calculation.

Calculations of the perfusion related values by the data processor 24 may be made in the manner described in U.S. Pat. No. 4,059,982 issued to Bowman and U.S. Pat. No. 4,852.027 issued to Bowman et al. (Thermistors of various shapes and characteristics may be substituted for the round thermistor bead analyzed in these patents. The general iterative mode of calculation will apply when using thermistors of various shapes and characteristics but analysis of the thermal characteristics of an individual thermistor will change with change in thermistor characteristics.) One such system of calculating perfusion useful in connection with this invention is illustrated by the flow chart of FIG. 2. In this system iterative calculations of intrinsic thermal conductivity and perfusion are made to obtain an accurate perfusion calculation. Data collected at the thermistor 12, which is related to effective thermal conductivity, is separated into its intrinsic thermal conductivity and perfusion components so that a measurement of perfusion is obtained. As indicated by block 50, the thermistor is energized to rapidly increase its temperature from a tissue baseline temperature (T1) to a second, predetermined temperature above tissue baseline temperature (T2). The heated thermistor transfers heat to the adjacent capillary bed. Subsequently, the temperature is caused to relax to the initial temperature (block 51). An intrinsic thermal conductivity value for tissue interrogated by the thermistor 12 is calculated (block 52) during a first time period at the initial portion of the heating cycle when the effects of perfusion are low. The calculation is based on the power required to energize the thermistor and assumes a zero value for perfusion. The calculated value of conductivity is then used to calculate a perfusion related value for tissue interrogated by the thermistor 12 during a second time period (block 53) when perfusion effects are high. The calculated perfusion value is used to recalculate the first obtained value for intrinsic conductivity (block 54). Using the recalculated intrinsic thermal conductivity value, the perfusion value is then recalculated at the second time period (block 55). Intrinsic thermal conductivity and perfusion recalculations are made iteratively (block 56) until the calculated values of perfusion converge to a substantially unchanging value.

In an alternate manner of making calculations indicative of endothelial function and the vascular health of a subject, data from the thermistor can be used to calculate two values for the effective thermal conductivity, one before and one after an intervention induces a change. These calculations are made without initially differentiating the constituent intrinsic conductivity and perfusion values. The intrinsic conductivity components of the measurements will be substantially constant for the time interval between the measurements. When the two successive measurements are compared, the substantially equal intrinsic thermal conductivity components cancel each other and the comparison yields a differential value that is the value for tissue perfusion in the capillary bed. That is any difference in the measurements is attributable to perfusion. In terms of the power used by the thermistor, the difference in power used or dissipated to maintain the predetermined elevated temperature of the thermistor when the two measurements are made is a function of the difference in the perfusion of the capillary bed that is interrogated by the thermistor during the measurements. The differential power value thus is indicative of endothelial function and of the vascular health of the subject.

Figure 3:
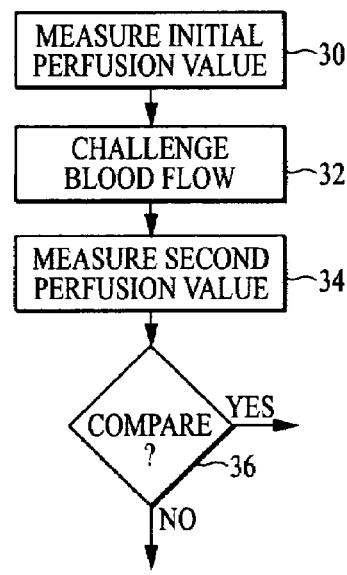
FIG. 3 is a flow chart illustrating a method according to the invention.

A method of assessing endothelial function in accordance with this invention will be described in connection with the flow chart of FIG. 3. As indicated by block 30, an initial measurement of perfusion is made to obtain an initial set of perfusion related data. For example, the sensor 10 is placed at a site on the forearm of a subject and an initial or reference tissue perfusion reading is made as described above in connection with FIG. 1 and FIG. 2. Blood flow to the site is then challenged as indicated by block 32, which challenge may be effected locally or systemically. Pharmaceuticals or other chemical agents can be used for local or systemic challenges. A blood pressure cuff may be used for locally challenging the blood flow. Perfusion may be monitored continuously throughout the assessment or individual measurements may be made before and after the challenge.

When a blood pressure cuff is used to produce a local challenge, it is applied promptly after the reference perfusion value is established. The cuff is located above the forearm, in the usual position on the upper arm, and inflated to constrict blood flow to the forearm site. The constriction is typically maintained for three to five minutes and quickly released. Immediately following the release of the blood pressure cuff a second set of perfusion related data is established and measured as indicated by block 34. The initial and second sets of perfusion related data are compared as indicated by block 36. The comparison will indicate the quality of endothelial function and whether peripheral cardiovascular disease is present, as previously described.

Figure 4:
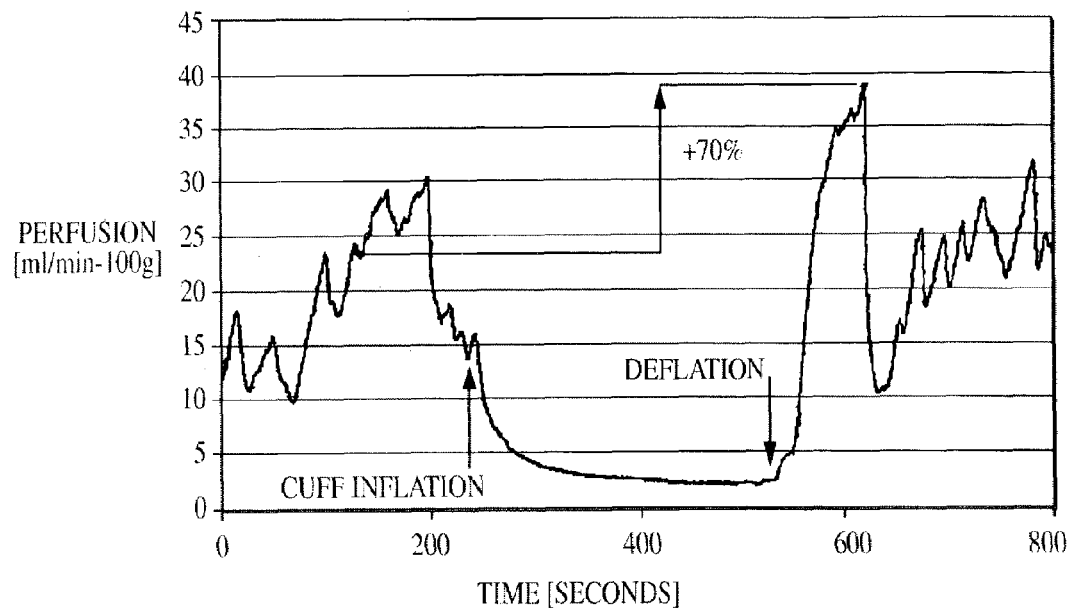
FIG. 4 shows perfusion values indicative of good endothelial function.
Figure 5:
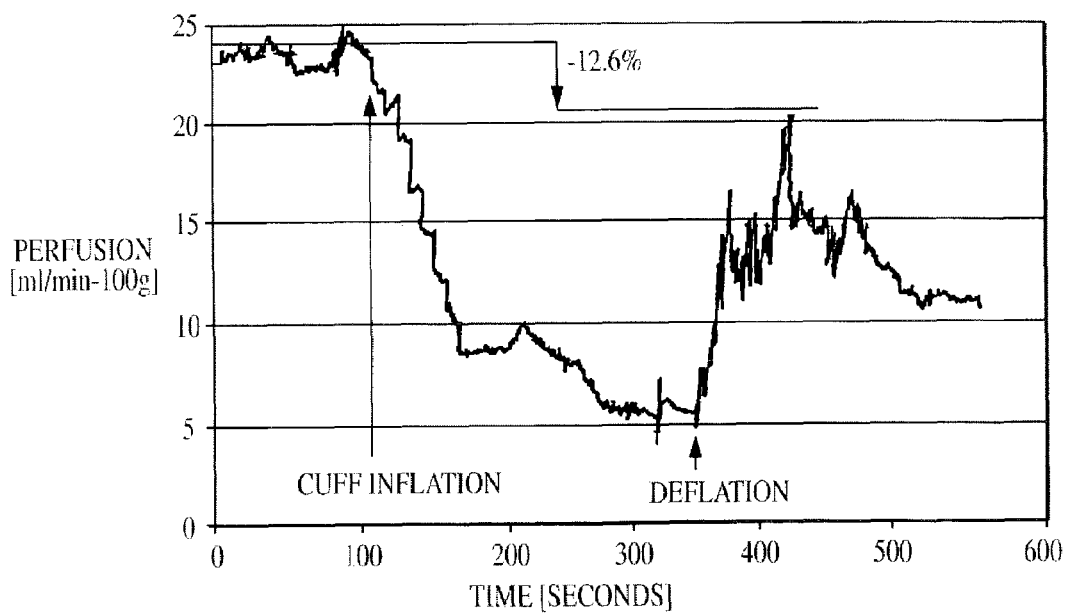
FIG. 5 shows other perfusion values indicative of poor endothelial function.

FIGS. 4 and 5 illustrate representative patterns of perfusion related data when monitoring is continuous through the entire assessment process. The characteristics of the pattern (for example, hyperemic response, slope, amplitude, mean values and vasomotor activity) are indicative of the state of endothelial function. FIG. 4 is one example of a plot of perfusion versus time representative of a subject with no coronary artery disease. Perfusion was measured on the forearm on the skin surface before, during and after a five minute inflation of a blood pressure cuff. The characteristics of the data pattern shown by the plot indicate good endothelial function and an absence of coronary artery disease. The pronounced hyperemic response after deflation of the cuff as compared to perfusion before inflation (+70%) is one such indicator. Significant vasomotor activity shown both before and after inflation of the cuff is also an indicator. FIG. 5 is a plot of perfusion versus time in a subject with demonstrated coronary artery disease. Again, perfusion was measured on the skin surface of the forearm before, during and after a five-minute inflation of a blood pressure cuff. The characteristics of the data pattern shown by the plot indicate poor endothelial function and a degree of coronary artery disease. The incomplete hyperemic response and the associated decrease in perfusion after deflation of the cuff as compared to perfusion before inflation (−12.6%) is one such indicator. The lack of appreciable vasomotor activity before and after inflation of the cuff also indicates poor endothelial function.

Chemical challenges to peripheral blood flow operate similarly to mechanical challenges. The sensor 10 is located at a selected site on a subject and perfusion is monitored before, during and after the challenge. Perfusion related data obtained before and after the challenge is compared, as with the mechanical challenge. Nitroglycerine and acetylchlorine are agents that can be used for a chemical challenge and ones to which the endothelial cells within the vascular system will respond in predictable ways. For example, the administration of nitroglycerine to a subject with a healthy endothelial function will produce vasodilatation and increased perfusion. Administration to a subject with poor endothelial function will produce vasoconstriction and reduced perfusion. Any vasodilator or vasoconstrictor will produce similar results. When a pharmacological agent is administered the reactivity of the blood vessel is a function of the health of the endothelial function of the subject. Pharmacological agents such as nitroglycerine can be administered systemically or locally. Local administration is found to have a local effect.

In summary as to the above examples, a subject with no peripheral vascular disease and good endothelial function will typically produce a characteristic data pattern distinguishable from the data pattern resulting from examination of a patient with coronary artery disease and poor endothelial function. Data produced by an examination can be processed to provide an output value that corresponds to the state of the endothelial function of the subject. Alternately, a medical practitioner may read the data resulting from the examination to evaluate endothelial function. For example, if data characteristics corresponding to good endothelial function are present (such as, a transient perfusion value after termination of a challenge substantially higher than the value of the initial perfusion measurement, a steep slope in the post-challenge plot and/or data indicating good vasomotor activity) a conclusion of good endothelial function is indicated. In contrast, a patient with coronary artery disease and poor endothelial function will characteristically produce, for example, one or more of an incomplete hyperemic response, a less steep slope and/or data indicating poor vasomotor activity.

When data is collected before and after a challenge to blood flow, either absolute or relative perfusion values will provide good results since the difference in the perfusion values before and after the challenge is the significant information. Absolute values may be indicated when data is processed or the processed data may indicate relative values. In either case, the results can be used to screen subjects for disease.

Figure 6:
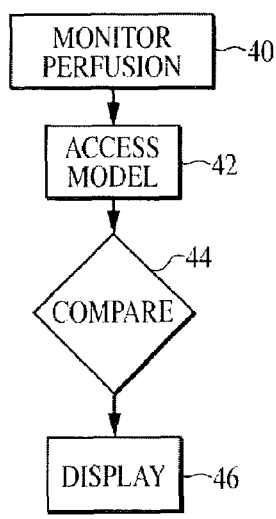
FIG. 6 is a flow chart illustrating another embodiment of the invention.

According to another embodiment of the invention a model of peripheral tissue perfusion is used as the reference data to which measured perfusion values for a subject are compared. The model, for example, may consist of perfusion related values or a pattern of perfusion related values characteristic of a subject with good endothelial function. The model can be used in lieu of an actual perfusion measurement in the subject. Measured perfusion is compared to the model to obtain data indicative of the health of the subject in so far as endothelial function is concerned. A method of assessing endothelial function in accordance with this embodiment is described in connection with the flow chart of FIG. 6. The sensor 10 is located at a selected site on the skin surface of the subject and, as indicated by block 40, perfusion is monitored as described above in connection with FIG. 1 and FIG. 2. As indicated by block 42, a model based on typical perfusion data for a healthy subject is accessed. Peripheral perfusion data supplied by the model is compared in a data processor to peripheral perfusion data from the subject. See block 44. Difference values resulting from the comparison are related to endothelial function. Values indicating endothelial function and peripheral vascular health are then displayed, as indicated by block 46.

Figure 7:
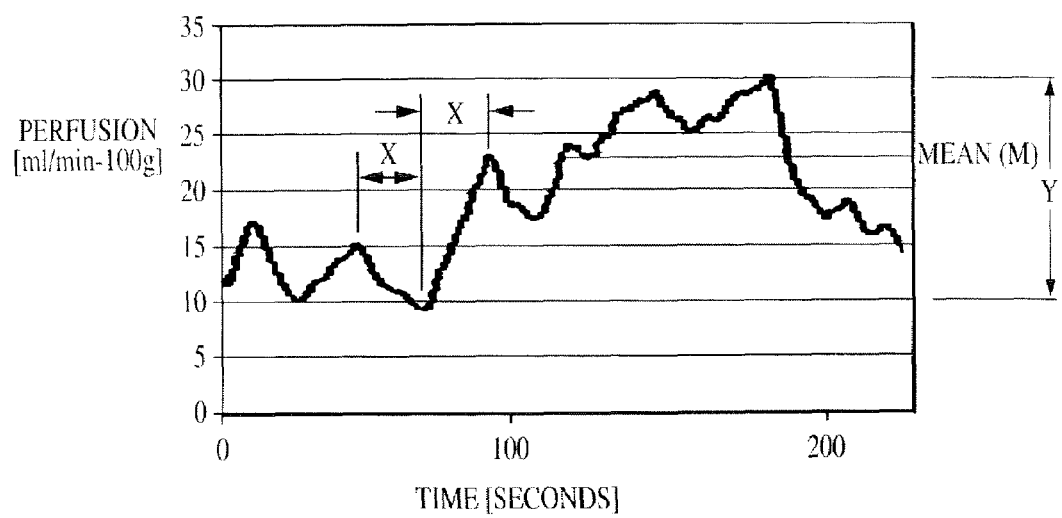
FIG. 7 illustrates typical perfusion variations with time in a healthy subject.

FIG. 7 illustrates a possible model relating peripheral tissue perfusion to endothelial function. The model is based on typical perfusion related values over time for a healthy subject; for example slope (x), amplitude (y) and mean (m) values. By way of example, greater amplitudes are indications of a healthy endothelial function and lesser amplitudes indicate lack of a healthy endothelial function. Patient data characteristics, such as amplitude and mean values, can be analyzed and compared to the corresponding data characteristics from the model. Data recognition techniques such as neural networks and feature-space analysis and many statistical analysis techniques can be used to compare characteristics of patient data to the model data. Patient data in close conformity with model data indicate healthy endothelial function. On the other hand, patient data that varies significantly from the model data (i.e., data having substantially lower amplitude and/or mean values) indicate poor endothelial function and corresponding pathology. A simpler model can be one in which preselected perfusion related values representative of a healthy endothelium are compared to measured values. Information similar to that illustrated in FIG. 7 could also be expressed as an algorithm for processing subject data.

Figure 8:
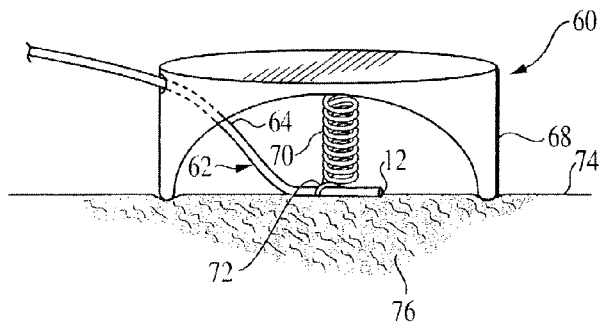
FIG. 8 shows schematically a perfusion sensor according to this invention.

FIG. 8 is a schematic diagram illustrating one example of a sensor constructed in accordance with this invention. The sensor 60 incorporates a probe 62 including a catheter 64 with a thermal transducer 12, such as a thermistor, at the distal end. The probe 62 is supported in a mounting device 68 by a resilient spring structure attached to the catheter 64 by coupling device 72. The spring structure may be a coil spring 70 as indicated, a leaf spring or any one of various other resilient devices. The spring 70 in any of its possible configurations is a constant force spring that exerts a predetermined force on the transducer 12 when the mounting device 68 is applied to the skin surface 74.

The thermal transducer 12 may be of the types described in U.S. Pat. No. 4,059,982 issued to Bowman and U.S. Pat. No. 4,852,027 issued to Bowman et al. The transducer is held to the skin surface 74 by the force of the spring 70 when the mount 68 is in contact with the skin surface. The mount may contact the skin surface along a path surrounding the transducer 12. The contact footprint may be continuous or discontinuous along a series of discrete contact loci. The contact pressure between the transducer 12 and the skin surface 74 is of a magnitude that accomplishes two mutually antagonistic results. It overcomes thermal contact resistance between transducer and the skin surface to establish effective thermal contact between the transducer and the skin surface and it avoids substantial capillary collapse in the capillary bed 76 underlying the skin surface. The transducer 12 interrogates a tissue volume in the capillary bed (i.e., the thermal response zone of the transducer). The mount 68 transmits the contact load to the skin surface and the underlying tissue. The mount 68 contacts the skin surface away from the thermal response zone of the transducer so as not to significantly alter capillary flow in the thermal response zone of the thermistor. The sensor 60 may be manually held to the skin surface or attached in any convenient manner. For example, a foam tape jacket could be used to attach the sensor to the skin surface and insulate the transducer from the ambient temperature.

Figure 9A:
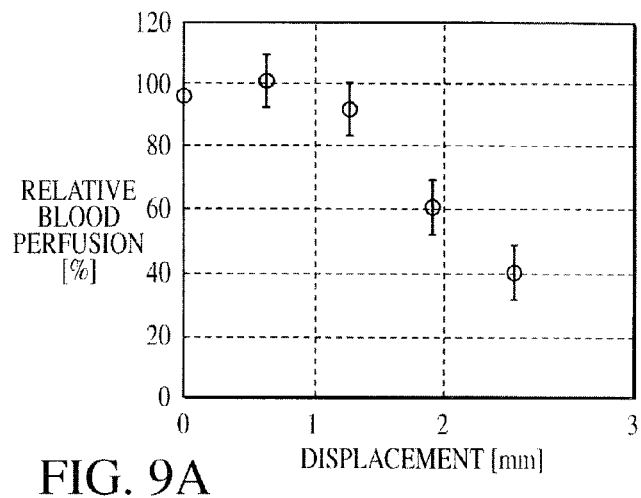
FIGS. 9A and 9B show the relationship of tissue perfusion in a capillary bed as a function of, respectively, sensor displacement into compressed tissue and pressure incident on the capillary bed.
Figure 9B:
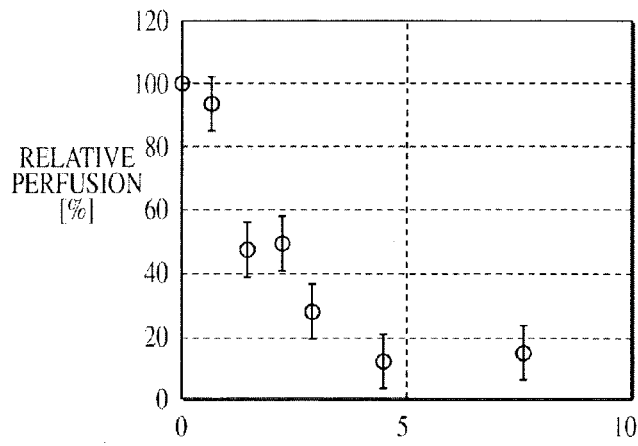

When the sensor is placed in contact with the tissue, the sensor pressure is controlled by spring 70 to achieve both low thermal contact resistance (i.e., effective thermal contact) between the transducer and the skin surface and an insignificant artifactual decrease in local tissue blood flow. Biomechanically, transducer contact pressure must be less than the sum of the connective tissue compressive strength and the pressure for capillary collapse. FIG. 9A shows the results of a study of relative surface perfusion measured as a function of transducer displacement. Transducer displacement is defined as displacement of the transducer into the compressed tissue from the original tissue surface location. Blood flow (perfusion) is relatively constant for the first 1.25 millimeters of transducer displacement and drops significantly after 1.5 millimeters of displacement. It was noted with interest that the data show a slight peak in the relative perfusion at a transducer displacement of about 0.6 millimeter. This may indicate that this displacement and the corresponding pressure are close to optimal. FIG. 9B shows the results of a study of relative surface perfusion measured as a function of applied pressure. Perfusion is relatively constant below 0.5 mmHg and decreases from capillary collapse at higher pressures.

Figure 10:
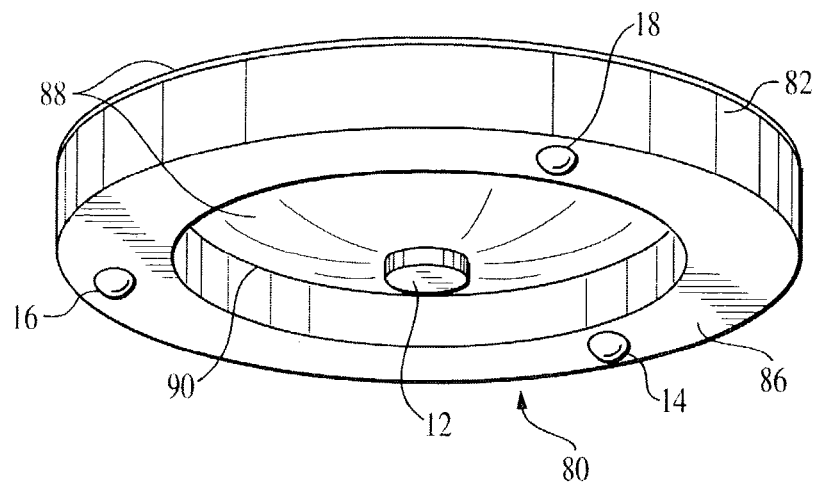
FIG. 10 is a perspective view a perfusion sensor according to this invention.

FIG. 10 illustrates one embodiment of a non-invasive sensor 80 constructed in accordance with this invention. The sensor 80 includes a flat polystyrene, thermally insulating, mounting ring 82 with a heat thermistor 12 mounted in the center. The mounting ring 82 defines a surface 86 for contact with the surface of the skin of a subject when the sensor 80 is in use. The thermistor 12 is supported on a member 88 connected along its outer edges to the mounting ring 82 at a surface 90 of the ring opposite the surface 86. The member 88 may be a circular inflatable bladder with the thermistor 12 mounted in its center. The bladder can be inflated more or less to cause the transducer to transmit, respectively, more or less pressure to the skin surface and the underlying capillary bed when the surface 86 is applied to the skin surface.

The degree of inflation of the inflatable bladder can be selected to cause the thermistor 12 to apply a desired contact pressure to the skin surface. Differing skin surface and capillary bed conditions may be found at different tissue locations or in the tissue of different subjects. Accordingly, the magnitude of the predetermined contact pressure that can be tolerated by tissue without degrading sensor performance can vary in different tissue locations and in different subjects. In each circumstance, the thermistor or other thermal transducer needs to be in effective thermal contact with the skin surface but not under a force which will produce pressure on the skin surface sufficient to collapse the underlying capillary bed.

As an optional feature, a number of temperature sensors 14, 16 and 18 are mounted at substantially equal intervals, in a triangular configuration, on contacting surface 86 of the ring 82. The diameter of the ring 82 is such that radial displacement of the temperature sensors 14, 16 and 18 from the thermistor 12 locates them outside the thermal response zone of the thermistor. This avoids thermal interference between the thermistor 12 and the temperature sensors 14, 16 and 18. The temperature sensors passively monitor tissue temperature around the thermal response zone of thermistor 12. In the calculation of perfusion values, temperature information from the temperature sensors 14, 16 and 18 is used to compensate for fluctuations in baseline temperature or changes in the thermal gradient.

Use of the sensor 80 will be described. The sensor 80 is placed on the skin of a subject so that the surface 86 is in contact with the skin surface. The thermistor 12, as well as sensors 14, 16 and 18, are then also contact the skin surface. The bladder member 88 applies to the thermistor 12 a force determined by the extent to which the bladder member 88 is inflated. The force applied to the thermistor 12 determines the magnitude of the contact pressure applied by the thermistor to the skin surface. The bladder inflation and the corresponding contact pressure are determined to have two significant effects. The contact pressure is of sufficient magnitude to reduce or minimize thermal contact resistance between the thermistor and the skin surface thereby to produce effective thermal contact between the thermistor and the skin surface. The magnitude of the pressure also is ineffective to produce substantial collapse of capillaries in the capillary bed within the interrogation zone of the thermistor. The flexibility of the bladder 88 also permits the thermistor 12 to position itself according to the skin surface contour and thereby make better thermal contact with the skin surface.

The thermistor 12 is energized for interrogating the capillary bed within the thermal response zone of the thermistor. The thermistor senses the thermal response of the tissue to the application of heat. Perfusion is calculated as a function of the power used by the thermistor, in the manner described above in connection with FIGS. 1 and 2. The temperature sensors 14, 16 and 18 sense baseline temperatures and provide data that can be used to compensate for shifts in baseline temperature.

Figure 11:
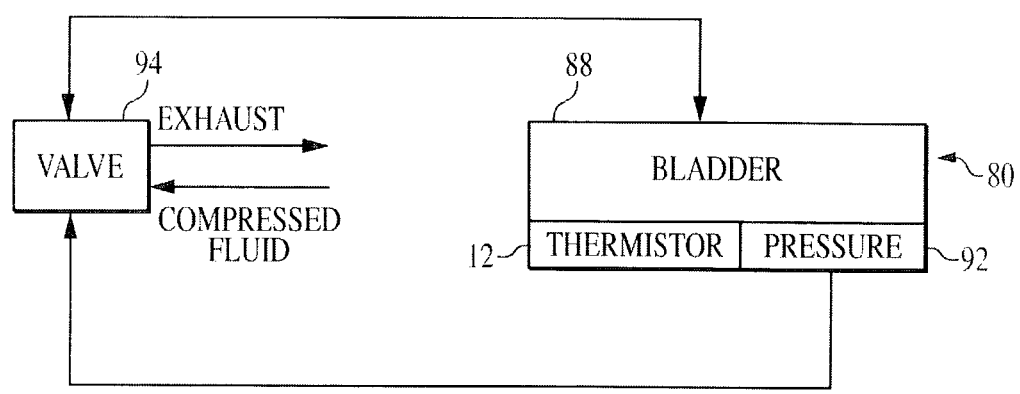
FIG. 11 is a schematic diagram of a control system for the perfusion sensor of FIG. 10.

As indicated by FIG. 11, a pressure sensor 92 may be employed with the thermistor 12 for sensing the skin contact pressure and adjusting the inflation of the inflatable member 88 to optimize the pressure applied by the transducer to the skin surface.

When the sensor 80 is applied to the skin surface of a subject, the pressure sensor 92 provides data to a servomotor controlled valve 94. The valve admits compressed fluid to the bladder 88 or exhausts fluid from the bladder in accordance with pressure data provided. The inflation of the bladder 88 and thus the pressure applied by the thermistor 12 to the tissue surface can be changed in accordance with tissue conditions and skin surface characteristics.

The invention claimed is:

1. Apparatus for non-invasively assessing endothelial function in a living subject comprising:
   a thermistor adapted to be placed on the skin surface at a selected location on the body of a subject for transferring thermal energy to the capillary bed adjacent the skin surface without substantial collapse of capillaries in the capillary bed;
   a controller for energizing said thermistor for an interval before and after a challenge to the blood flow to the capillary bed to transfer thermal energy from said thermistor to the capillary bed during the intervals;
   a data processor for quantifying tissue perfusion in the capillary bed as a function of the dissipation from the capillary bed of thermal energy transferred by said thermistor;
   a comparator for comparing tissue perfusion in the capillary bed before and after the challenge to blood flow.

2. Apparatus according to claim 1 further comprising means for applying to said thermistor pressure effective to establish thermal contact between said thermistor and the skin surface at the selected location and ineffective to significantly impair blood flow in the capillary bed adjacent the skin surface at the selected location.

3. Apparatus for assessing endothelial function of a subject comprising:
   a thermistor for applying thermal energy to a selected location on the skin surface of a subject and sensing the temperature at the selected location;
   control means for energizing said thermistor to heat the capillary bed adjacent the selected location to a predetermined temperature above the baseline temperature of the capillary bed and subsequently causing the temperature of the capillary bed to relax to the baseline temperature of the capillary bed, the power dissipated by the thermistor in heating the capillary bed being a function of the perfusion in the capillary bed;
   a data processor for providing a value corresponding to perfusion in the capillary bed as a function of the power dissipated by the thermistor;
   a data storage system for storing values provided by said data processor; and a comparator for indicating systemic endothelial function using a stored value obtained prior to a constriction of blood flow to the selected location and a value corresponding to perfusion in the capillary bed resulting from the constriction of blood flow to the selected location.

4. An apparatus for assessing endothelial function in a living subject comprising:
   thermal transducer means for applying thermal energy to the skin surface of a subject and detecting the thermal response to the application of thermal energy;
   means for applying to said transducer means pressure sufficient to produce thermal contact between said transducer means and the skin surface of a subject and insufficient to produce substantial collapse of capillaries in the capillary bed adjacent the skin surface;
   means for producing signals functionally related to the thermal energy applied by said transducer means and the thermal response to the application of thermal energy;
   data processing means for calculating a tissue perfusion related value using the signals produced by said signal producing means;
   data storage means for storing perfusion related data obtained during a condition when blood flow to the capillary bed is unchallenged;
   means for comparing perfusion related data stored by said data storage means and perfusion related data obtained during a condition when blood flow to the capillary bed is challenged; and
   means responsive to said comparing means for providing information indicative of endothelial function.

5. An apparatus for assessing endothelial function in a living subject wherein blood flow to a selected location on the body of the subject is constricted for an interval comprising:
   thermal transducer means for applying thermal energy to the skin surface at the selected location and detecting the thermal response to the application of thermal energy;
   means for applying to said transducer means pressure sufficient to produce thermal contact between said transducer means and the skin surface and insufficient to produce substantial collapse of capillaries in the capillary bed adjacent the skin surface;
   means for producing signals functionally related to the thermal energy applied by said transducer means and the thermal response to the application of thermal energy;
   data processing means for calculating a tissue perfusion related value using the signals produced by said signal producing means;
   data storage means for storing perfusion related data obtained prior to the interval;
   means for comparing perfusion related data stored by said data storage means and perfusion related data obtained after the interval and resulting from the constriction of blood flow to the selected location; and
   means responsive to said comparing means for providing information indicative of endothelial function.

\* \* \* \* \*